United States Patent [19]

Orazio, Jr. et al.

[11] Patent Number: 5,032,734

[45] Date of Patent: Jul. 16, 1991

[54] METHOD AND APPARATUS FOR NONDESTRUCTIVELY MEASURING MICRO DEFECTS IN MATERIALS

[75] Inventors: Fred D. Orazio, Jr., Centerville; Robert B. Sledge, Jr., Dayton; Robert M. Silva, deceased, late of Dayton, all of Ohio, by Ruby M. Silva, Executrix

[73] Assignee: VTI, Inc., Dayton, Ohio

[21] Appl. No.: 597,857

[22] Filed: Oct. 15, 1990

[51] Int. Cl.$^5$ .............................................. G01N 21/01
[52] U.S. Cl. ..................................... 250/572; 250/225
[58] Field of Search ................ 250/562, 563, 572, 225; 356/338, 340, 341, 368, 369, 370, 429–431, 445–449

[56] References Cited

U.S. PATENT DOCUMENTS

| | | | |
|---|---|---|---|
| 3,574,470 | 4/1971 | Vukelich et al. | 250/572 |
| 3,652,863 | 3/1972 | Gaskell et al. | 356/239 |
| 3,904,293 | 9/1975 | Gee | 356/448 |
| 4,015,127 | 3/1977 | Sharkins | 356/369 |
| 4,314,763 | 2/1982 | Steigmeier et al. | 356/237 |
| 4,342,515 | 8/1982 | Akiba et al. | 356/239 |
| 4,352,016 | 9/1982 | Duffy et al. | 250/358.1 |
| 4,352,017 | 9/1982 | Duffy et al. | 250/358.1 |
| 4,391,524 | 7/1983 | Steigmeier et al. | 356/338 |
| 4,395,122 | 7/1983 | Southgate et al. | 250/572 |
| 4,575,249 | 3/1986 | Grieger | 356/446 |
| 4,575,249 | 3/1986 | Grieger | 356/446 |
| 4,672,196 | 6/1987 | Canino | 356/369 |
| 4,845,356 | 7/1989 | Baker | 356/368 |
| 4,873,430 | 10/1989 | Juliana et al. | 250/228 |
| 4,904,877 | 2/1990 | Pietzsch | 250/572 |
| 4,933,567 | 6/1990 | Silva et al. | 250/572 |
| 4,978,862 | 12/1990 | Silva et al. | 250/572 |

OTHER PUBLICATIONS

F. D. Orazio, Jr., W. K. Stowell and R. M. Silva, Instrumentation of a Variable Angle Scatterometer (VAS), Aug., 1982.
W. K. Stowell, R. M. Silva and F. D. Orazio, Jr., Damage Susceptibility of Ring Laser Gyro Class Optics, Aug. 1982.
R. M. Silva, F. D. Orazio, Jr. and W. K. Stowell, Scatter Evaluation of Supersmooth Surfaces, Aug. 1982.
IBM Technical Disclosure Bulletin, vol. 20, No. 8, Jan. 1978, Automatic Brewster's Angle Thin Film Thickness Measurement Spectrophotometer, Chwalow, et al.

Primary Examiner—David C. Nelms
Assistant Examiner—S. Allen
Attorney, Agent, or Firm—Jacox & Meckstroth

[57] ABSTRACT

A method and apparatus are disclosed for nondestructively measuring the density and orientation of crystalline and other micro defects on and directly below the surface of a properly prepared material such as a semiconductor wafer. The material surface is illuminated with a probe beam of electromagnetic radiation which is limited to a nondestructive power level or levels. Polarization and wavelength or wavelengths of the electromagnetic radiation are selected according to certain characteristics of the material so that penetration depth is controlled. Specific orientation of the material with respect to the probe beam and the detector is required to detect that portion of the probe beam scattered from the defects of interest, surface or subsurface, without interference from other scatter sources and to identify the orientation of the defects. Maps of scatter intensity versus position are made according to the density of the defects encountered.

6 Claims, 8 Drawing Sheets

METHOD AND APPARATUS FOR NONDESTRUCTIVELY MEASURING MICRO DEFECTS IN MATERIALS

Related Applications

This application is a continuation-in-part of application Ser. No. 437,109, filed Nov. 16, 1989, which is a continuation-in-part of application Ser. No. 301,721, filed Jan. 26, 1989, which is a continuation-in-part of application Ser. No. 218,542, filed July 13, 1988, abandoned, which is a continuation-in-part of application Ser. No. 918,518, filed Oct. 14, 1986, abandoned, which is a continuation-in-part of application Ser. No. 724,966, filed Apr. 19, 1985, abandoned.

BACKGROUND OF THE INVENTION

Many of the materials used in the manufacture of semiconductors, optics and a variety of other applications require the highest quality material available to meet the performance requirements expected in the future. This is particularly important when it relates to the quality and cleanliness of the surface, and the crystalline structure, defects and impurities in the material. In the case of semiconductors like silicon and gallium arsenide for instance, crystalline defects or impurities on or near the surface of the material can significantly degrade the performance of electronic components and integrated circuits made from that material, or keep them from operating at all. Material defects in optics made from semiconductors, glasses and metals can have catastrophic results when used with high powered lasers or when second order optical effects are being used. These situations have been recognized for some time, and a variety of equipment has been disclosed or developed to measure the surface character of these special materials. For example U.S. Pat. No. 4,314,763, entitled "DEFECT DETECTION SYSTEM", discloses one of several techniques used to measure surface defects and contamination on semiconductors.

The measurement of the crystalline and other micro defects directly below the surface, however, has been much more difficult. For example U.S. Pat. No. 4,391,524, entitled "METHOD FOR DETERMINING THE QUALITY OF LIGHT SCATTERING MATERIAL", similar to the one previously mentioned, discloses one technique developed for that purpose. A second approach is described in U.S. Pat. No. 4,352,016, entitled "METHOD AND APPARATUS FOR DETERMINING THE QUALITY OF A SEMICONDUCTOR SURFACE" and U.S. Pat. No. 4,314,017, entitled "APPARATUS FOR DETERMINING THE QUALITY OF A SEMICONDUCTOR SURFACE". All of these measurement techniques have significant limitations when measuring subsurface crystalline damage and other micro defects, both surface and subsurface, which are most important to the improvement and use of these materials.

The term defects, as used herein, refers to any of a variety of structural crystalline defects found near the surface in bulk material or in layers or thin films, either grown-in or processing induced, like slips, dislocations, stacking faults and even buried scratch traces as well as defects which are formed when foreign material is incorporated into the crystal structure such as inclusions, precipitates and impurity clusters and other impurity related defects. Likewise non-crystalline structural defects that occur in amorphous and polycrystalline materials such as voids, buried scratches and pits, and the interface between layers either purposely deposited or formed during processing are included. The term defects is also used to describe surface features such as pits, scratches, scuffs, pinholes and exposed impurity clusters, inclusions and bubbles as well as particles and other surface contamination.

Basically, there are three ways of generating defects in the materials of interest. First, defects can be incorporated into the material when it is manufactured in its bulk form. For instance, when single crystals of silicon or gallium arsenide are grown, dislocations can form in the boule due to thermal stresses induced during the growing process, or when impurities in the starting material, and from other sources, are incorporated into the crystal. For polycrystalline and amorphous materials, impurities can easily come from the starting materials, the preparation tools that come in contact with the material and even the gases in the environment where the materials are being made. Bubbles and inclusions are also formed during the melting and cooling process.

Secondly, after the material is manufactured, it must be cut into usable pieces and the surfaces ground and polished in preparation for further processing. These steps of cutting, grinding and polishing also introduce slips, dislocations and more impurities into the crystal structure just below the prepared surface as well as surface defects like pits and scratches. Polycrystalline and amorphous materials have the same problems with surface defects. They can also have subsurface defects caused by the high pressures used in grinding and polishing. These buried defects form as part of a layer of material at the surface, which under pressure has either recrystallized or become amorphous, and the bulk of the material. Impurities can also be introduced into the material during these operations by diffusion and other mechanisms. In the case of semiconductors, this second class of defects, those that are processing induced, is generally 1,000 to 1,000,000 times greater in number than the defects grown into the original boule of material. Not only are the numbers larger, but as stated, these defects are all located near the surface while the grown-in defects are distributed throughout the volume of the material.

Thirdly, defects such as stacking faults, precipitates, dislocation lines and ion implantation induced defects can be generated by various fabrication processes typically used in the processing of semiconductor wafers. The same is true of optical and other materials not only for crystalline defects but also for the buried defects which can be generated in amorphous and polycrystalline materials by the preparation processes. Fabrication processes such as coating, etching, ion implantation and cleaning can all cause surface and subsurface defects. These defects will affect the way light is transmitted through or reflected from an optical material and can affect the properties of electronic materials. Another effect, which is just beginning to be understood, is the connection between subsurface defects of all types and the defects in coatings deposited on the surface. It has long been known that substrate surface defects can cause flaws in the thin film coatings placed on them. Subsurface defects are more subtle in that they are very difficult to detect nondestructively but can be equal to surface defects in causing flaws in the coatings. Since optics, electronics and many other applications make extensive use of coatings, such effects are of great importance. For instance, epitaxial layers grown on semiconductor wafers can have stacking faults grown-in during the manufacturing process and these can be related to the defects already existing in the substrate wafer.

One technique currently used to measure crystalline damage is described in U.S. Pat. Nos. 4,352,016 and 4,352,017. This approach measures the reflectance of ultraviolet light, at two wavelengths, from the surface of a semiconductor wafer. This technique is known to be insensitive to damage at any depth in the material primarily because of the use of ultraviolet light which is a shallow penetrator in semiconductor materials. A second factor significantly limiting sensitivity is the reflectance measurement itself. Such measurements are notoriously difficult to make and result in looking for small variations in large numbers, which is one of the reasons why this technique requires measurements at two wavelengths. The practical application of this reflectance technique shows up these deficiencies.

A second approach is described in U.S. Pat. No. 4,391,524. This approach can measure the light scattered from the surface and subsurface regions but because of the geometry of the measurement, important data is lost. There are three factors which bear on this assessment which are independent of the wavelength selected for the probe beam. First, the angle of incidence of the probe beam is 0°. This eliminates any possibility of determining the directional nature of the defects, or of using polarization to help discriminate between surface and subsurface defects. Secondly, the detector subtends a large solid angle thus integrating scatter from all directions, again making impossible the determination of directional defects, and at the same time diluting the signature of the defects it is designed to measure. And finally, the detector line of sight is also at 0°, or near 0°. This introduces significant amounts of surface scatter into the measured signal which is nearly impossible to separate from the subsurface scatter under these conditions. Subtle variations in surface scatter will mask the scatter from the subsurface that are the purpose of the measurement. The result is a measurement that is insensitive to oriented defects, which most subsurface defects are, and even insensitive to many very small surface defects which are also oriented.

Other techniques which purport to measure surface and/or subsurface defects using a scatter measurement technique all measure the total integrated scatter from the surface of the test part. This technique known as TIS integrates the scatter from the surface and subsurface as well as from all directions. The result is an insensitive measurement of mostly surface roughness for which this technique was originally designed. The surface scatter component of the total scatter from a material is very large, and will overwhelm the subsurface component if the scattered light is collected anywhere near the specularly reflected beam. Also, many very small surface defects such as pits and particles are faceted so that the scatter is generally large in one direction and nonexistent in all the others. For large pits and particles the integration that takes place does not dilute the signal, but for the very small pits and particles, the integrated signal from TIS will not show a noticeable change.

All of the scatter measurement techniques available for the nondestructive detection of surface defects are limited in that they are not able to accurately detect defects below about 1 micron in size unless the defects are uniformly shaped, spherical or hemispherical. Real defects, especially particles, are not uniformly shaped but are faceted or oblong or are some unusual shape. These odd shaped defects do not scatter light uniformly and can not be accurately detected by such techniques. In fact, only a small fraction of such defects can be detected by these techniques.

SUMMARY OF THE INVENTION

The object of the present invention is to improve significantly the capability of measuring the density of surface and subsurface crystalline and other micro defects in semiconductors, optics and other special materials and coatings. The present invention is directed to a nondestructive method of measuring the density and orientation of crystalline or other micro defects on and directly below the surface of a material which allows penetration of electromagnetic radiation by measuring the radiation scattered from the defect sites. In accordance with the invention, the material to be measured must have a low surface roughness and must be clean so that the surface scatter does not contribute significantly to the total scatter signal if subsurface measurements are desired. The material must be illuminated with a beam of electromagnetic radiation preferably from a laser or other high intensity single wavelength source. A properly selected polarization and wavelength are required so that the penetration depth of the radiation is controlled. The geometry of the measurement is particularly important for best results. For highly transparent materials, the natural bulk scatter of the material must not significantly exceed the scatter from the defects of interest. Also the thickness of the part must be large enough to separate the scatter from the front and back surface unless both surfaces are of interest as in certain special applications. This separation is dependent on the measuring field of view of the detector. For thin transparent parts that are polished on both sides, the scatter from the front and back surface will overlap and cannot be easily separated. In this case the total scatter will give an overall evaluation of both surfaces, the subsurface associated with each surface, and the bulk scatter. If the bulk scatter is small, this type of evaluation of the surface and subsurface combined can be very useful. The intensity of the beam must be sufficient to provide a scatter intensity large enough to measure from a given depth, for subsurface measurements. However the power density of the beam should not be so high that damage is done to the material being measured.

It is also possible to use multiple selected wavelengths to simultaneously detect defects at different depths. By separating the scatter signals for each wavelength and subtracting the signal of the shallow penetrating wavelengths from that of the deeper penetrating wavelengths, it is possible to do depth gradient defect detection. In effect, detecting a zone of defects at some depth while eliminating the effects of the defects nearer the surface. This can also be done by changing the laser intensity since a higher intensity will put more power at a greater depth thus allowing the detection of defects at a greater depth.

The incident angle of the beam, the viewing angle of the detector, the polarization of the beam and the polarization of the detected radiation are used to enhance the scatter signature from the defects of interest, and at the same time minimize scatter from unwanted sources on or in the material. The relative rotation of the material with respect to the probe beam is used to determine the orientation of the defects and enhance the scatter signature from the oriented defects. This relative rotation can also be used to minimize scatter from a known defect orientation on or in the material, in order to enhance the scatter from defects that are not oriented or are oriented in a different direction. For instance, on diamond turned parts, selecting an orientation parallel to the scribe marks left by the diamond turning will eliminate the high scatter associated with these marks and allow detection of other, much smaller, defects on or below the surface. Another application of this approach could be used to examine semiconductor wafers before and after ion implant to detect the extent of the damage caused by the ion implant process. For this application, the wafer would be measured and the rotational position would be selected to minimize the scatter from the polishing induced subsurface defects which are highly oriented. The wafer would then be ion implanted which will introduce new subsurface defects. These defects are not oriented but are random in nature. The wafer would be measured again with the rotational position selected to minimize the scatter as before. A comparison between the first measurement and the second will yield a number related to the density of defects introduced by the ion implant. The purpose here is to minimize the effect of the polishing induced subsurface defects in order to detect the defects caused by the ion implant alone. This same approach could be used with any process that introduces randomly oriented surface or subsurface defects.

The measurement technique of the invention is particularly useful for measuring the processing induced defects in and on the surface of single crystal semiconductor materials such as silicon, gallium arsenide, indium phosphide and mercury cadmium telluride as well as generally transparent optical materials such as quartz and sapphire. Defects in and on polished metal surfaces can also be detected but the detection depth is limited for such materials. The technique is also useful in detecting real particles, pits and other surface defects, less than 1 micron in size, on semiconductor wafers, optics and other highly polished surfaces like plated magnetic and optical disks used for computer data storage.

In order to use the data generated by such a system constructed in accordance with the invention, it is desirable to plot and display the data in the form of a map of the defects. This can be done by substituting color variations for scatter intensity variations and plotting these color variations on the map according to the X and Y coordinate of the scatter measurement. By adjusting the color distribution on a map, certain features can be brought out or enhanced. For instance, isolated impurity clusters just below the surface will show up as individual high scatter spots which in many cases are higher than the background scatter level. These spots can be isolated as a single color with a high contrast to show their distribution. Many such displays are possible as specific defects are associated with a specific scatter signature. Black and white maps can also be made using shades of gray as an indicator of scatter intensity. Mapping may also be defined as storing the data in a computer for later analysis. Such analysis may be very complex and not require the display of a map. The result may be a number or series of numbers, or even an electronic signal to another computer, other equipment or a human operator.

Other features and advantages of the invention will become apparent from the following description, the accompanying drawings and the appended claims.

DESCRIPTION OF THE PREFERRED EMBODIMENTS

Figure 1:
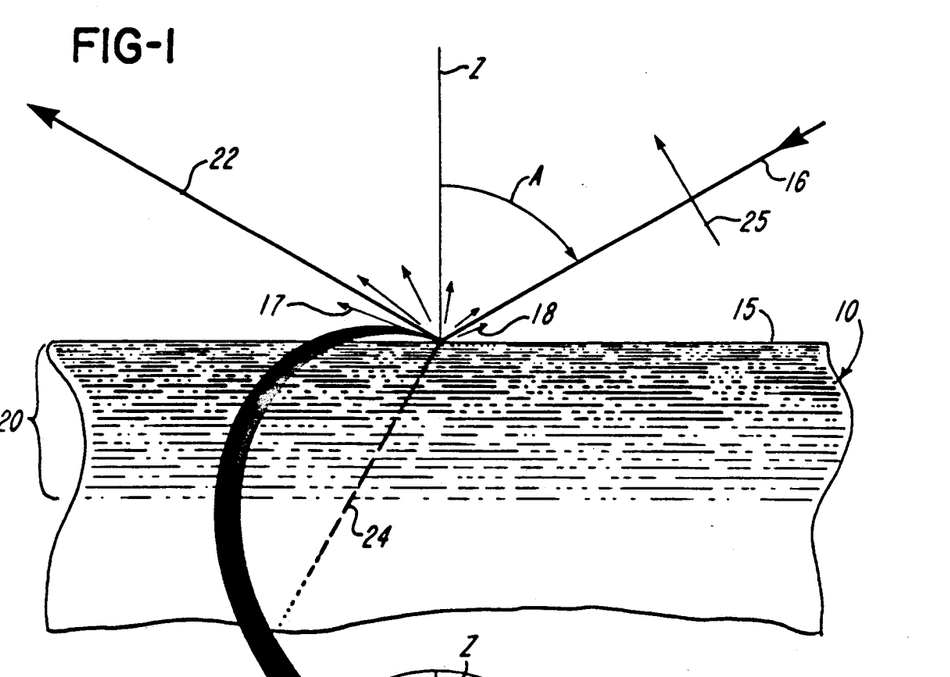
FIG. 1 is a greatly enlarged cross section of a material with surface and subsurface defects being illuminated by a beam of electromagnetic radiation in accordance with the invention.
Figure 1A:
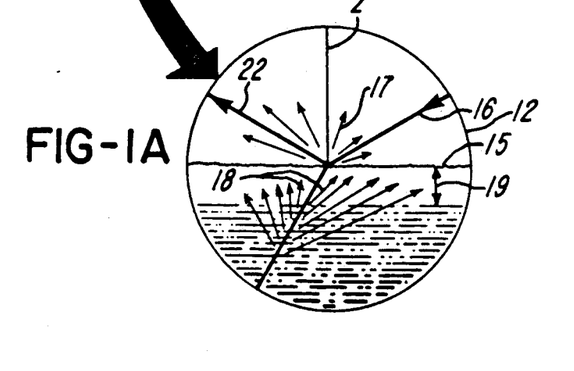
FIG. 1a is an enlarged portion at the intersection of the beam and the material.

FIG. 1 and FIG. 1a show a material or test part 10, such as an optic or a semiconductor wafer, having a surface 15 illuminated by a beam 16 of electromagnetic radiation directed at an angle of incidence A. The material or part surface 15 to be measured should be smooth with only a microroughness present as shown in the enlargement 12 in FIG. 1a. For example, at a wavelength L of 632.8 nanometers, a root mean square (rms) microroughness on the order of 0.005 times L, or about 30 angstroms or less, typically insures that surface scatter 17 does not overpower the near subsurface scatter 18. Also, the surface 15 must be clean in order to prevent the scatter due to surface contamination from overpowering the scatter 18 from the subsurface defects unless the measurement of surface contamination is the desired result. When looking for isolated surface defects, the same surface roughness criteria apply. In any case, the general surface roughness should be at a low enough level that background surface scatter is not a significant portion of the signal.

For the measurement of subsurface defects, the incoming beam 16 has a wavelength, polarization, intensity and angle of incidence designed to optimize the transmission into the material 10 to a chosen depth. This increases the scatter 18 from the subsurface while decreasing the scatter from the surface 17. The wavelength is selected by examining a material property, the extinction coefficient k, so that the penetration depth of the radiation $L/(2 \pi k)$, where pi is the well known constant (3.14159), is greater than the depth of the defects in the subsurface defect zone 20, but shallow enough so that the radiation does not penetrate to the back side of a thin part. As an example, the processing defects in a silicon wafer typically extend to no more than 2 or 3 micrometers and certainly no more than a few tens of micrometers, while the wafer thickness is on the order of 350 to 400 micrometers. At the same time, a beam with a wavelength of 632.8 nanometers will have a penetration depth in silicon of about 3.7 micrometers. For thick parts the material can be transparent to the wavelength used, k can be very small. In this case the limitation is the level of the natural bulk scatter of the material. If the level of bulk scatter is significantly higher than the scatter from the surface and/or subsurface defects of interest, then accurate measurements will be very difficult.

The penetration depth gives a relative indication of how far below the surface the probe beam will penetrate before being completely extinguished. The actual detection depth, the depth at which significant defects can be seen by their scatter signatures, is roughly proportional to the penetration depth. The detection depth, for a given wavelength, is strongly related to the energy density (power/area) of the probe beam at the surface, the sensitivity of the scattered light detector system and the other physical parameters of the system such as polarization, angle of incidence, detected solid angle and the system signal-to-noise ratio which, in this instance, is defined as the detected scatter signal divided by the total system noise.

The polarization for subsurface defect detection is selected for minimum intensity in the reflected beam 22 and maximum intensity in the transmitted beam 24. For all cases, the maximum transmitted intensity is yielded by P polarized light. The P in this case refers to the state where the electric vector 25 of the incident radiation 16 is parallel to the plane of incidence. This insures that the intensity of the transmitted beam 24 is maximized and thus the scatter 18 from the subsurface defects is maximized.

Other polarizations can be used to achieve a variety of results. For instance, if S polarization is used (S in this case refers to the state where the electric vector is perpendicular to the plane of incidence), the reflected intensity is maximized and the transmitted intensity is minimized thus enhancing the surface scatter 17 over the subsurface scatter 18. This polarization is used for the detection of surface defects.

It is possible to combine S and P polarization to get circular polarization. Circular polarization, in this case, refers to the state where the electric vector is uniform in length and rotates about the direction of propagation of the wave in either a clockwise or counterclockwise motion. A circularly polarized beam can be considered half P polarized and half S polarized. A uniformly unpolarized beam would have the same effect. Using such an arrangement for the probe beam would result in both P and S polarized scattered light being sent to the detector. By separating the scattered light into its P and S components and using a separate detector for each, surface and subsurface defects could be measured simultaneously. Another variation on this approach would be to use elliptically polarized light where the rotating electric vector is not uniform in length and the S and P components are not equal. This would be done to tailor the ratio of surface to subsurface scatter desired for a given input power.

The intensity of the incident beam 16 must be sufficient to provide a subsurface scatter intensity 18 large enough to measure at the depth of interest. Since the intensity drops off rapidly with depth, it is possible to control the detection depth by adjusting the intensity. The energy density of the beam at the surface (power/area) must not approach the damage threshold of the material being examined however. Even low power beams, when focused to a tight spot, can have energy densities which can cause a large charge buildup on the surface sufficient to damage the crystal structure in some materials, thus creating the very defects being measured.

The angle of incidence A can be varied between 0° and 90°. Typically, large angles of incidence provide the best results because the penetrating electromagnetic radiation interacts with the lineated subsurface defects which act like a grating and scatter the light back out through the surface. The blown-up view 12 of FIG. 1A is to give a better understanding of what the real surface and subsurface are like and to show the increasing density of defects with depth. The low defect zone 19 is a region between the surface and the heaviest zone of defects often described as the M-layer in semiconductors and the Beilby layer in optics. It is an area of recrystallized or amalgamated material which can shield the subsurface defects, that this invention measures, from ordinary detection.

Figure 2:
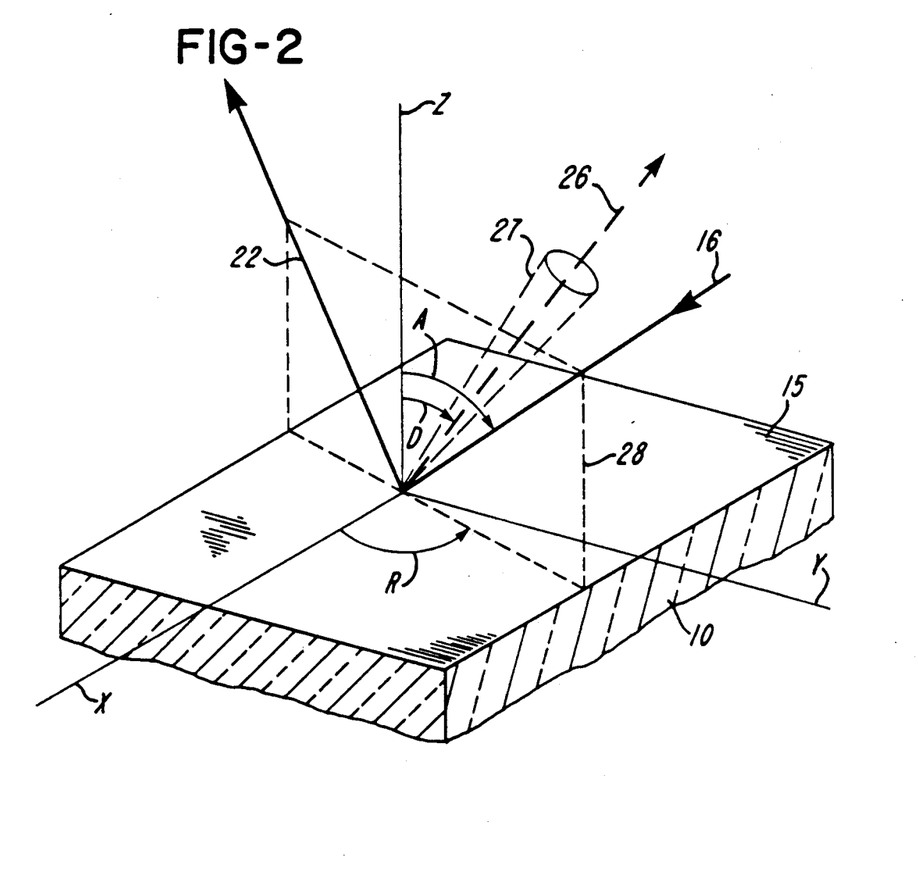
FIG. 2 is a perspective view of the material surface and schematically illustrates the orientation of the beam and the detector line of sight relative to the material surface.

FIG. 2 shows a schematic of the surface 15 of the part 10 under test. The X, Y and Z axes are shown with the Z axis perpendicular to the surface 15. The incoming beam 16 has an angle of incidence A. The line of sight 26 of a detector (not shown) is determined by the angle D. The incident beam 16, the reflected beam 22, the detector line of sight 26 and the Z axis are all in the same plane 28. The angle made by the plane 28 with the X axis is the angle R. The Z axis, the incident beam 16 and the detector line of sight 26 all intercept at the same point on the surface of the test part, the point being measured.

For subsurface measurements the angle of incidence A of the beam 16 should be as close as possible to Brewster's angle (the angle of minimum reflectance at P polarization, sometimes called the polarizing angle) in order to maximize the amount of energy transmitted into the material, and at the same time minimize the energy scattered from the surface. As an example, Brewster's angle for silicon is about 75°. Typically, angles of incidence larger than 55° begin to cause problems because the impact point of the incident beam 16 begins to spread across the surface. The reflectance of P polarized light at a wavelength of 632.8 nanometers and an angle of incidence of 55°, is about 15%. This means that 85% of the light penetrates the material. In a practical sense, this percentage of light, with an energy density of 30 watts/cm$^2$ in a 0.25 mm diameter beam, will be able to detect defects in silicon that are 4 to 5 microns below the surface, when using a suitable detector. It is possible to reshape the beam cross section from circular to elliptical, with the major axis of the ellipse perpendicular to the plane of incidence, so that a more circular cross section will be projected on the surface at large angles of incidence. Other angles A, less than 55°, can be used but with poorer results in terms of signal-to-noise ratio which is used herein as the ratio of detected subsurface scatter power to total detected power.

For the detection of surface defects using S polarization, the angle of incidence A of beam 16 should also be large to maximize the amount of surface scatter and minimize the subsurface scatter. This is necessary because for any given material and a given wavelength of the incident beam polarized S, the greater the angle of incidence, the greater the reflectance. Since there is no "Brewster's angle" for S polarization, the largest angle possible should be selected. As a matter of convenience in the design and construction of equipment, Brewster's angle could be used and the polarization switched from S to P depending on what kind of defects are being measured, surface or subsurface. Again, using circularly polarized, or uniformly unpolarized, light would allow surface and subsurface defects to be measured simultaneously as long as there is a separate detector for each polarization.

The angle D of the detector line of sight 26 should be positioned in the direction opposite the reflected beam 22. The angular difference between A and D should be small, less than 30°, for large values of A, and large, greater than 30°, for small values of A. This is true because the energy which is scattered from the subsurface must traverse some thickness of material (19 in FIG. 1A) and emerge from a high index to a low index. This causes a severe refraction of the scattered light toward the surface 15 of the material 10 being tested, especially for high index materials such as semiconductors. Other angles D and A may be used but with poorer results in terms of signal-to-noise ratio. Values of D which place it near the specularly reflected beam 22, increase the surface scatter component of the detected signal to the point where the subsurface measurements cannot be made with great accuracy.

The line of sight 26 of the detector is of great importance to the invention because the solid angle 27, that is intercepted by the detector, is small in comparison with other measurement techniques. In most scatter measurement approaches, the scatter is gathered from a large solid angle. This has the effect of integrating or averaging the scatter signal over the large solid angle. In effect, this averaging approach dilutes the particular kind of information that is important in the measurement of surface and subsurface defects, and that is the R angle position information. This is an important enhancement of the scatter signature because the defect sites act like a grating and force the scatter in one particular R angle direction while virtually eliminating the scatter from all other directions. A large solid angle 27 will integrate and dilute this angular information. The invention described herein will operate best when the solid angle intercepted by the detector is less than 0.1 and preferably between 0.001 and 0.01 steradians.

In the case of highly transparent materials, the measurement field of view must also be restricted so that natural bulk scatter and extraneous scatter from other surfaces will not be detected and distort the result. The normal approach is to limit the field of view of the detector by placing a field stop in the detector optics, but other approaches can be used to solve this problem. In some situations, as with thin transparent parts with both surfaces polished, the scatter from the back surface of the part may be of interest. For this case a larger field of view may be necessary to allow detection of scatter from both surfaces and the subsurface. The effect of the natural bulk scatter of the material must be considered for this situation.

The angle R of the plane of incidence 28 is very important in determining the orientation of the subsurface defects in a particular material. The nature of the subsurface defects in many materials is in the form of lineations which are generated by the processes of sawing, grinding, polishing and even cleaning. These lineations are in the form of zones of defects which are significantly longer than they are wide. In effect, these lineations form a fine grating. Hence the scatter from these features is highly oriented so that when the plane of incidence 28 is perpendicular to them, the scatter is very intense in the plane of incidence. At any other angle, the scatter is significantly less or nonexistent in the plane of incidence. This means that the angle R is directly related to the orientation of the subsurface defects. By selectively examining the scatter intensity versus angle R, the direction of maximum scatter, and hence the orientation of the defects, can be determined. This directionality can then be directly related to the process used to form the surface. Thus effects of process variations can be directly observed. Ideally, an angle R and the maximum scatter associated with it would be determined for each position on the material.

Other positions for the angle R may also be important from a crystallographic perspective. For instance, certain kinds of defects, like stacking faults, are oriented in certain crystallographic directions. Therefore it would be appropriate, if detection of this particular type of defect was important, to chose the R angle corresponding to this particular known direction so as to detect the stacking faults while minimizing the effects of other defects. There are other situations where there is a known direction that must be avoided because the signal from that direction will overwhelm the signal from the defects of interest. This is the case when measuring diamond turned parts. The scribe marks left in the surface and subsurface by the diamond turning are so large that the signal from them will not allow smaller defects to be detected. By avoiding the direction that is perpendicular to the scribe marks and concentrating on the direction parallel to the scribe marks, small surface and subsurface defects can be detected. A similar approach can be used when looking for subsurface defects caused by ion implants. In this case the minimum scatter direction is selected because the ion implant defects are randomly oriented. This has the effect of minimizing the scatter from the polishing induced subsurface damage. Other variations on the use of the R angle are possible such as when looking for a second maximum or other second order effects which would be overlooked by using only the maximum R angle position.

When looking for isolated surface defects, the R angle is also very important. Many surface defects, especially particles whose maximum dimension is less than the wavelength L of the probe beam and which are irregular in shape, will scatter significant amounts of energy in only one narrowly defined R angle direction. By examining the variations in the scatter versus the R angle at a given spot, it is possible to detect these particles or other defects even though they are much smaller than the wavelength L of the probe beam.

The scatter detector can be a solid state device or a photomultiplier type of device. In any case it is possible to chop or pulse the beam to enhance detection of the scatter signal, a technique well known in the art. This may be necessary when examining very high quality single crystal material to achieve the highest possible signal-to-noise ratio.

Individually the aspects of the invention just discussed, the angle of incidence A, the detector line of sight angle D, the Z axis angle R and the solid angle intercepted by the detector 27, are only moderately useful in improving the scatter signature from subsurface defects. Taken together, these four aspects of the invention greatly improve the sensitivity of the measurement apparatus to the most subtle variations of subsurface defects. Each embodiment of the invention described in the following paragraphs, is chosen to take special care to enhance the ability of the apparatus to make the best possible use of these elements of the present invention.

Figure 3:
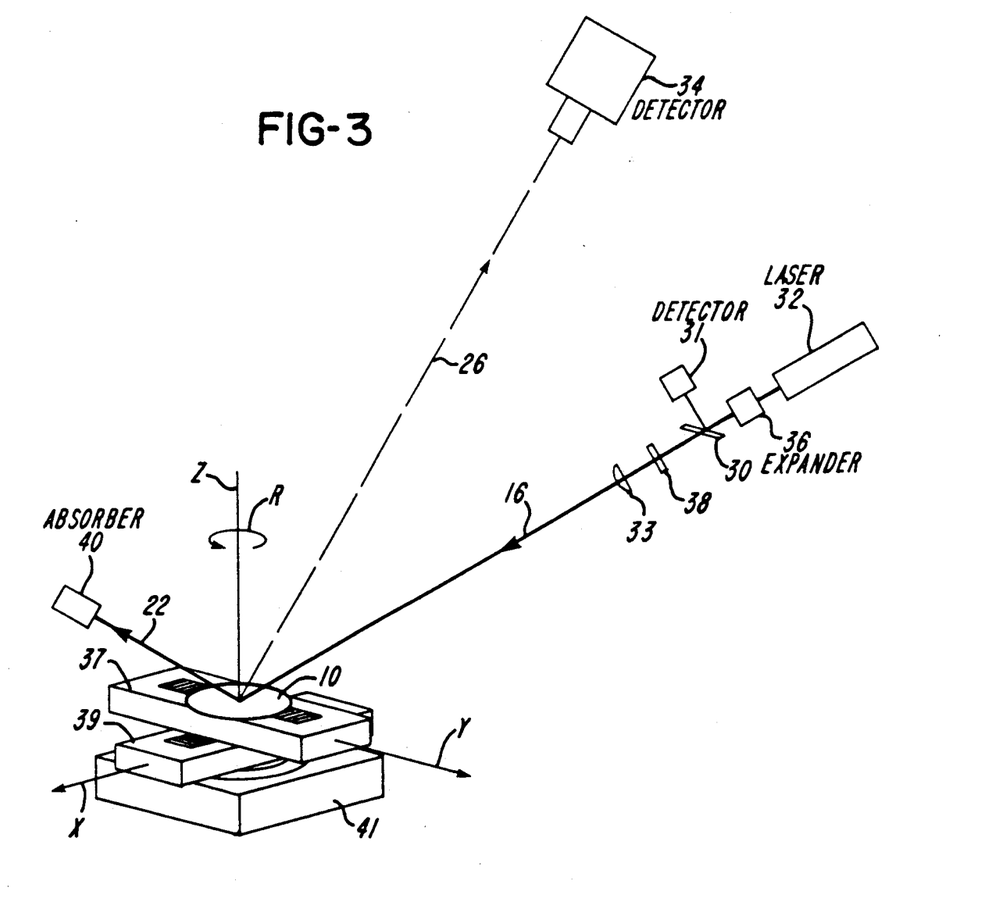
FIG. 3 illustrates an embodiment of the invention wherein the material moves under a fixed beam and a fixed detector.

The following figures are major embodiments of the present invention. The first is shown schematically in FIG. 3. In this embodiment a source of electromagnetic radiation or laser 32 and the detector 34 are fixed, and the test part 10 is moved in the X and Y directions and rotated about the Z axis. The detector 34 may be a photomultiplier tube or a solid state detector. The various motions of the test part are accomplished with computer controlled, motor driven micropositioning stages 39 and 37 for motion along the X and Y axes respectively and stage 41 for rotation about the Z axis. The three stages are assembled so that the Z axis always intercepts the test surface at the intersection of the X-Y coordinates being measured. At each X and Y position the angle R is varied from 0° to 360°, a maximum reading is taken with the detector 34, fed to a computer, and a map of the maximum scatter intensity versus position is generated. This is only one of many possible sets of data. Maps from directions other than the maximum, or multiple directions, can also be mapped. These maps are the output of the measurement device of the invention. The beam 16 is conditioned prior to interacting with the test part 10. A spatial filter/beam expander 36 gives the beam a Gaussian cross section and focuses the beam to a given diameter at the test part surface, to increase the energy density to a level suitable for the measurement. Other beam cross sections are acceptable and may even perform better such as a tophat which has a constant intensity across the beam diameter, but the Gaussian cross section is acceptable and is the easiest to generate. A polarizer 38 insures the correct polarization, S or P, depending on whether surface or subsurface defects are to be measured. Combinations of S and P polarization are possible but in this case the detector must be able to select the polarization of interest or the result will be a combination of surface and subsurface effects. Beamsplitter 30 divides the beam so that a small portion of the energy is directed to detector 31 the output of which is fed to the computer. This information is used to correct the output of detector 34 for variations in the input power from laser 32. Cylindrical lens 33 reshapes the beam cross section to an elliptical shape so that the foot print of the beam on the test part surface is circular. The reflected beam 22 is stopped with an absorber 40 to eliminate spurious reflections.

Figure 4:
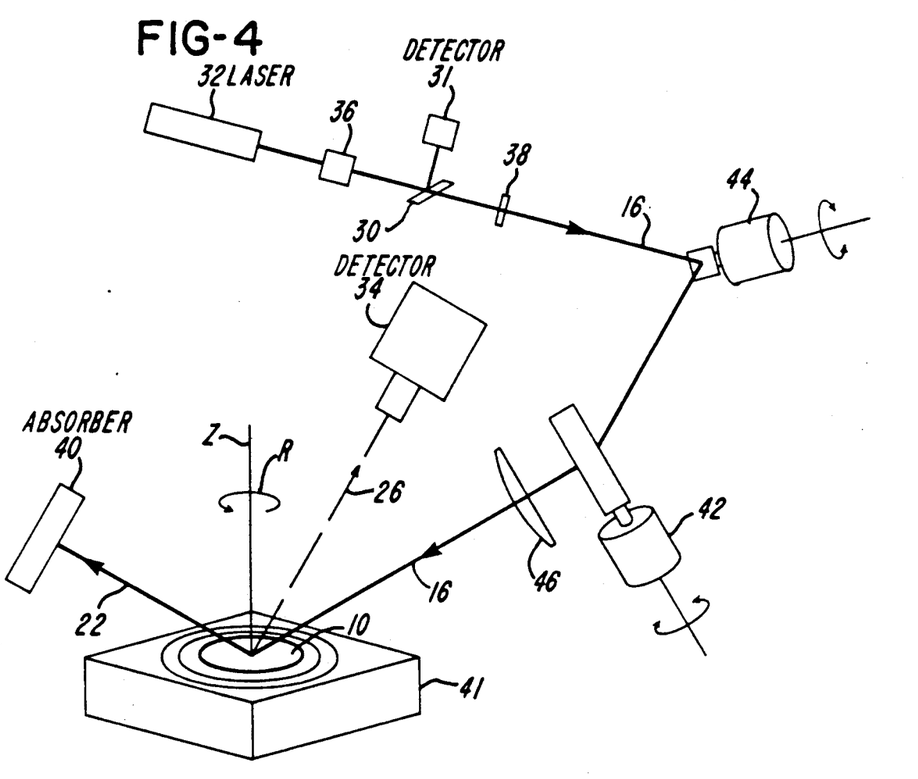
FIG. 4 illustrates an embodiment wherein the beam is scanned over the material laterally in the X and Y directions while the material rotates about the Z axis and the detector is fixed.

FIG. 4 is the schematic of an embodiment where the detector 34 is fixed and the test part 10 moves only in rotation about the Z axis, which is also fixed with respect to the test part 10. The probe beam 16 is scanned in the X and Y directions using movable mirrors 42 and 44 which oscillate in planes disposed at 90° to each other. A lens 46 corrects for angular beam variations caused by the scanning. The beam stop 40 is large to accommodate the scanned beam and insures that the beam does not reflect or scatter back to the detector and cause erroneous readings. With this arrangement, the scanning can be done very quickly over large areas. The angle R must still be changed, using micropositioning stage 41, by rotating the material under examination, but the material is fixed in the X and Y directions.

With the embodiment just described, it is not possible to locate an X-Y coordinate and then rotate about a Z axis through that particular point on the test part. The R angle must be fixed and the entire surface of the test part scanned in X and Y to get one complete map. This would require considerably more processing to obtain a final composite map or would be used when the orientation of the defects are known from previous measurements. In this arrangement, the detector field of view must encompass the entire scanned area for proper results.

Figure 5:
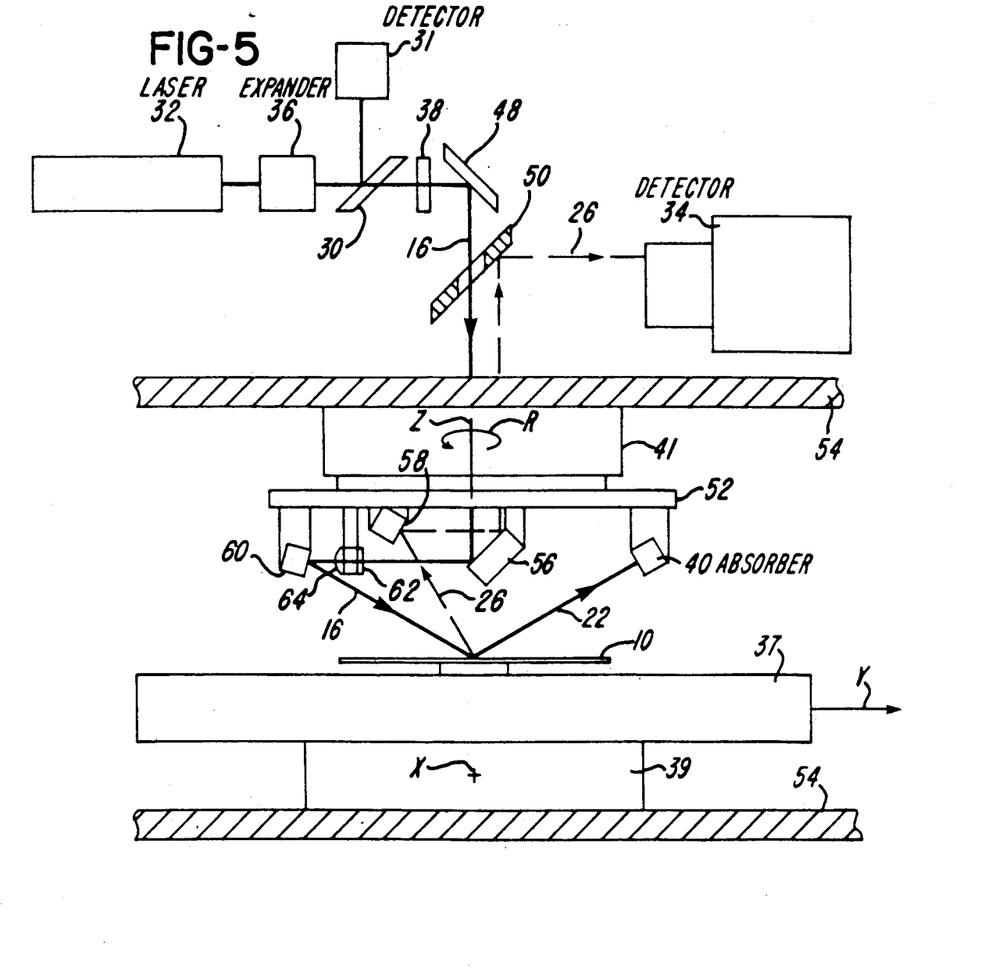
FIG. 5 illustrates an embodiment wherein the material moves laterally in the X and Y directions and the beam of electromagnetic radiation rotates about the Z axis.

FIG. 5 shows an embodiment wherein the test part 10 moves by means of micropositioning stages 39 and 37 in the X and Y directions and the beam is rotated about the Z axis with stage 41. This separation of axes simplifies the design in many respects particularly with respect to the lack of electrical connections to the rotating portion of the apparatus. The beam is generated by a laser 32 and conditioned as before except that element 38 converts the incident radiation to circular polarization. Then it is directed by steering mirror 48 through the center of annular mirror 50 and through a hole in the center of rotation stage 41. At this point the beam 16 is coincident with the Z axis. The beam is redirected by mirror 56 through polarizing filter 62, which now converts the incident radiation to the correct polarization, and cylindrical focusing lens 64. Finally the beam 16 impinges on mirror 60 which gives it the proper angle of incidence on the test part 10. The reflected beam 22 is intercepted by beam absorber 40. The scattered electromagnetic radiation is gathered by mirror 58 and reflected by mirror 56 through the hole in stage 41 to mirror 50 along path 26 to the detector 34. All the optical components on optical bench 52 rotate about the Z axis on the movable part of stage 41.

Figure 6:
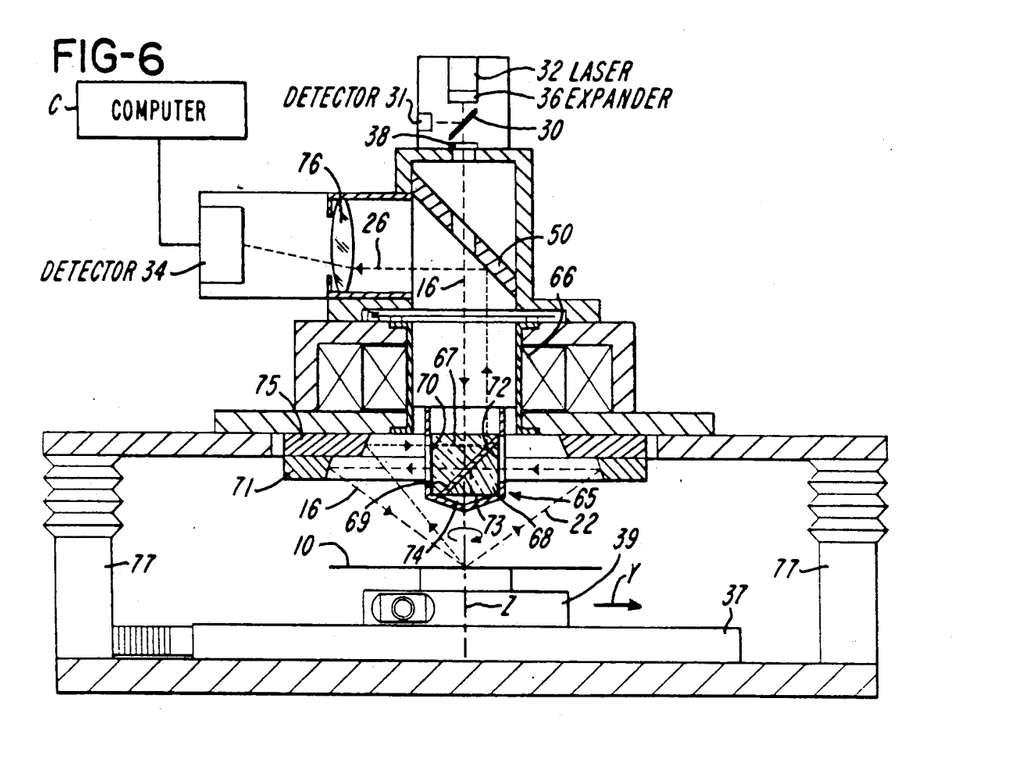
FIG. 6 illustrates an embodiment of the invention designed for very high speed mapping of semiconductor wafers or other flat surfaced materials.

FIG. 6 is an embodiment of the invention designed for high speed defect measurements on semiconductor wafers or other flat surfaced materials. In this case the test part 10 moves by means of micropositioning stages 39 and 37 in the X and Y directions and the beam is rotated about the Z axis by means of an air bearing supported optical element 65. The air bearing 66 allows the optical element to rotate at a very high speed and thus allows measurements to be made quickly. The probe beam 16 is generated by a laser 32, passes through optics 36 to filter and shape the beam as before. The optical element 38 converts the beam to circular polarization. The beam must be coincident with the Z axis which is the axis of rotation of the air bearing 66. The beam passes through the rotating optical element 65 which consists of two prisms 67 and 68 separated by an opaque material 69. The prism 67 reflects the beam at 90° to the Z axis and through the face of prism 67 which has a polarizing film 70 on the surface. This converts the circularly polarized beam 16 to a P polarized condition for subsurface measurements in this case. The beam is then reflected from annular mirror 71 to give it the proper angle of incidence on test part 10 and the reflected beam 22 travels back to mirror 71 and through the face of prism 68 which has a polarizing film 72 which only allows S polarized light through. The effect will be to reduce the intensity of the reflected beam 22 by a significant factor and convert the remaining light to S polarization. The beam is then reflected from the angled face of prism 68 and through the bottom face of prism 68 which has a polarizing film 73 which will only allow P polarized light through, again reducing the intensity of the beam. The remaining light impacts on the angled internal surface of rotating element 65 which has a black absorbing coating 74. The purpose of this part of the optical element 65, and the circuitous path for the reflected beam 22, is to eliminate any reflection of the probe beam back into the optical system where it might interfere with the measurement. For surface measurements, polarizing films 70, 72 and 73 would be set for S, P and S polarization respectively. The light scattered from the subsurface defects in the test part 10 is collected by annular mirror 75 and reflected back into rotating optical element 65 and back to annular mirror 50 along path 26. The light passes through focusing optic 76 and to detector 34. Vertical micropositioning stages 77 adjust the height of the rotating element 65 above the test part 10 to accommodate for any thickness variations between test parts. A computer C provides the data analysis and mapping function by converting the data to colors according to a preset scale and mapping the colors according to the X-Y coordinates on the part being tested.

Figure 7:
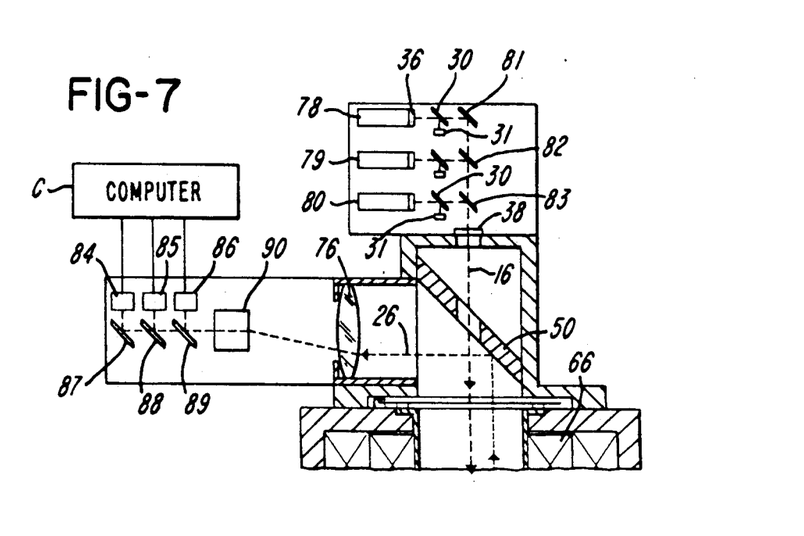
FIG. 7 illustrates an embodiment of the invention which is similar to FIG. 6 but which uses three wavelengths for the probe beam simultaneously.

FIG. 7 is an embodiment of the invention that is similar to that shown in FIG. 6 except that there are three lasers at different wavelengths and three detectors for those wavelengths. This embodiment of the invention is designed specifically for subsurface measurements. Each of the three lasers 78, 79 and 80 is operating at a different discrete wavelength. Each of the wavelengths is chosen to obtain noticeably different penetration depths in the material being measured. Each laser has a spatial filter/beam expander 36 to focus and filter the output, and a part of the beam, in each case, is split off by mirror 30 and captured by detector 31 to monitor the beam power. Mirrors 81, 82 and 83 are designed to be highly reflective at the wavelength of its corresponding laser while transparent at the other wavelengths. The result is a single beam 16 containing three discrete wavelengths which is circularly polarized by optical element 38. This single composite beam is reflected by rotating element 65 to annular mirror 71 and directed on to test part 10. The light at the three wavelengths is scattered back to mirror 75, through rotating element 65 and along path 26. The light is focused by lens 76 and collimated by optical element 90 and reflected to detectors 84, 85 and 86 by traverse mirrors 87, 88 and 89 which are again designed to reflect strongly at the wavelength selected but be transparent at the other wavelengths. Therefore, each mirror will reflect only one wavelength to its associated detector which is tuned and filtered for that wavelength. For example, mirror 89 will reflect a single wavelength to detector 86 while passing the other two wavelengths to the following two mirrors.

The effect of using two, three or more wavelengths in the measurement apparatus described, is to allow separate wavelengths to penetrate to different depths and be detected separately. Each detector receives a different signal containing the scatter signature of the defects from just below the surface to whatever depth that wavelength can penetrate in the material being tested. The wavelength that penetrates the least will contain the least information while the next deepest penetrating wavelength will contain all the previous information plus new information about deeper defects. If the shallower information is subtracted from the deeper information, the result will be just information about the deeper defects. If these depths are well known, then a zone of defects at a known depth can be identified. The same process can be continued with the next wavelength to obtain a third depth zone, the first being the one obtained by the shallowest penetrating wavelength alone and the second depth zone the one obtained by substracting the first from the second deepest penetrating wavelength. More or fewer wavelengths can be used depending on the amount of information desired and the complexity of the instrument one is willing to accept. The subtraction of information must be done with due regard to the rotational orientation of the defects since defect orientation can change with depth. The best approach is to take the rotational data for each wavelength at a given point and subtract it getting both a magnitude and direction for that point in the desired depth zone.

The benefit of this embodiment of the invention is to allow the determination of the depth of the defects accurately and nondestructively. This depth information is not available with the previous embodiments of the invention.

Figure 8:
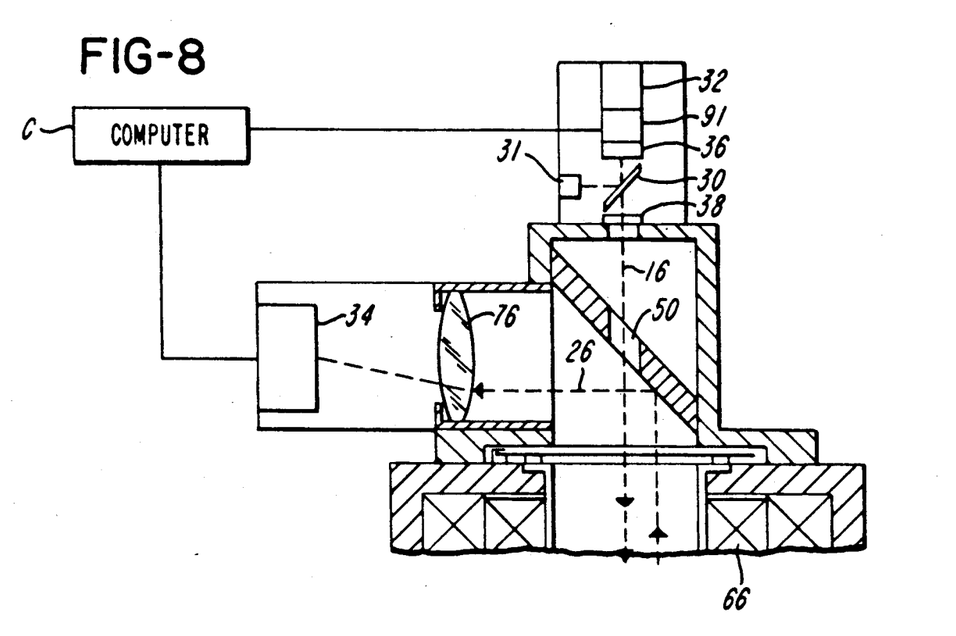
FIG. 8 illustrates an embodiment of the invention which is similar to FIG. 6 but which varies the power in the probe beam.

Another embodiment of the invention, shown in FIG. 8, allows defect depths to be determined in a different way. This embodiment is also very similar to that shown in FIG. 6, and is also designed specifically to measure subsurface defects. The difference being that laser 32 now has a power modulator 91 that is controlled by the computer C. This allows the power output of the laser to be changed and controlled so that different power levels can be available in the incident beam 16. Since the wavelength and power of the probe beam are selected to achieve a predetermined detection depth and the probe beam power decreases exponentially once it has entered the test material, lowering the power will reduce the detection depth. This is true because there is an absolute power level below which the power scattered from the defects that emerges from the surface is so small that it is below the noise level of the system. Hence changing the power level changes the detection depth.

This detection depth change with power can be used just the same as wavelength changes, as described for FIG. 7, are used to determine the depth of defect zones. In this case, however, the application must be slightly different. One possible way to apply this technique would be to actually make several passes over the test part, each at a different power level and then subtract the appropriate data to get the depth information. Another way would be to modulate the power level very rapidly so that at each rotational position two or more power levels are available. Each power level would be stored as a separate piece of data for that location on the test part. The data would then be appropriately subtracted to extract the depth information.

This approach has some advantages over the multiple wavelength approach described for FIG. 7. The resulting equipment is less complicated and therefore less expensive. It is possible to have computer control over the detection depth that is desired and the control is much finer in that slight variations in the detection depth are possible. The main difficulty is that increasing the detection depth by increasing the power can rapidly lead to power levels that will damage the test part, particularly semiconductor parts, because of the nonlinear nature of the absorption of light under the test conditions.

Another approach to be considered is the combination of the embodiments described for FIG. 7 and FIG.

8 which would involve adding modulator 91 to the lasers 78, 79 and 80 in FIG. 7. This would allow both multiple wavelengths and power levels to be combined to optimize the operation of the equipment for the material being tested and the defect depth desired.

Figure 9:
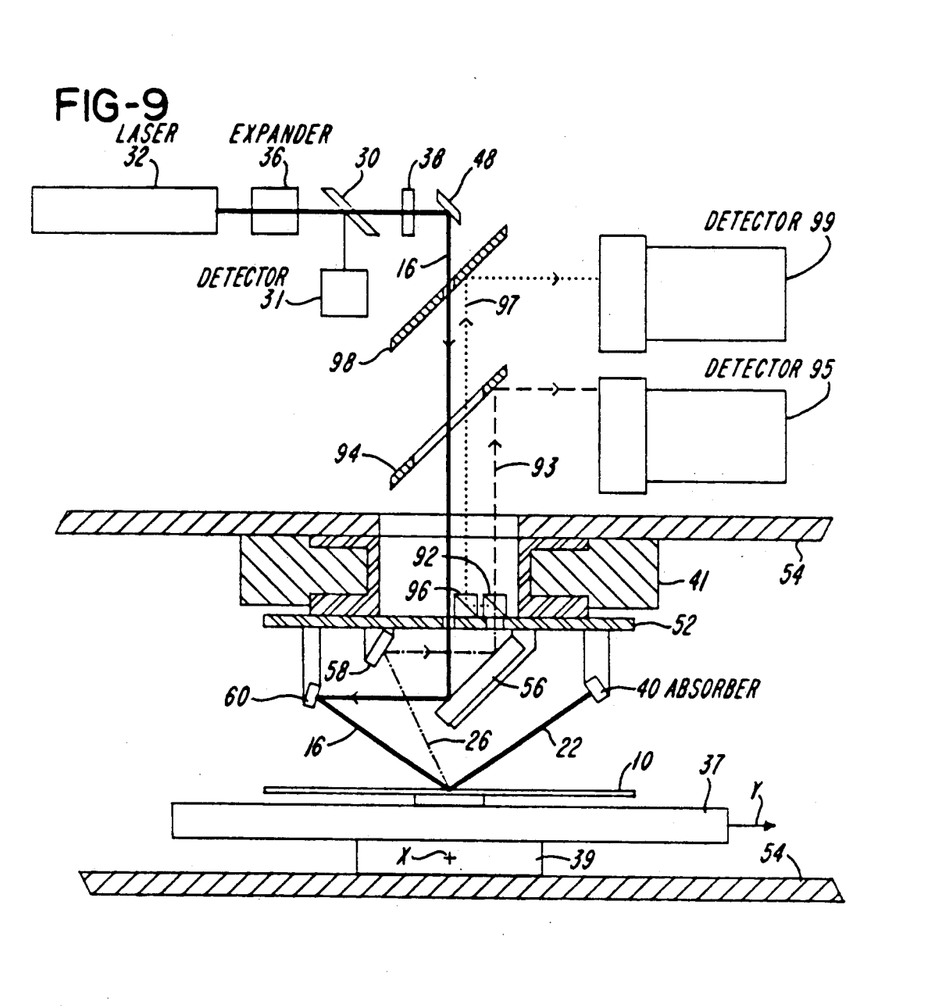
FIG. 9 illustrates an embodiment of the invention which is similar to FIG. 5 but which detects both surface and subsurface defects simultaneously.

FIG. 9 shows an embodiment of the invention which is in some ways similar to that shown in FIG. 5. The difference being that the circularly polarized probe beam 16 is not linearly polarized before impinging on the surface of the test part 10. The result is that the scattered light 26 contains both P and S polarized components. This scattered light is reflected by mirrors 58 and 56 up to polarizing beamsplitter 92. This beamsplitter will transmit only P polarized light and reflect only S polarized light. The P polarized scattered light 93 reflects from annular mirror 94 which has a large central opening. The light enters detector 95 which responds equally to P and S polarized light. As the optical bench 52 rotates on stage 41, the light entering detector 95 will change from P to S for every 90° of rotation of optical bench 52 even though the light exiting beamsplitter 92 is always P polarized with respect to the optical bench 52.

The light reflected from polarizing beamsplitter 92 is S polarized and is reflected again from polarizing beamsplitter 96. The S polarized scattered light follows path 97 and is reflected from annular mirror 98 which has only a small hole for the incident beam 16. The scattered light enters detector 99 which is identical to detector 95. The electrical output of detector 95 corresponds to the variations of the P polarized scattered light and the electrical output of detector 99 corresponds to the variations of the S polarized scattered light. This embodiment of the invention allows the simultaneous detection of S and P polarized light so that surface and subsurface defects can be detected from the same place on the test part.

Finally, when using P and S polarization together to examine the surface and subsurface simultaneously, the variations of scatter with R angle may be different for each polarization at a given spot. This may require a more complex analysis of the results to get an accurate representation of the location of the defects, surface or subsurface. Such an analysis may also effect the determination of the defect orientation. The result of this analysis would be a scatter signature which could be used to isolate the defects of interest for the particular material being examined.

All of the embodiments of the present invention should be isolated from the environment in two important ways. The apparatus should be vibration isolated to remove the effects of subtle movement between the probe beam and the test part. Vibrations will cause gross inaccuracies since adjacent portions of the test part may have vastly different scatter signatures. Also the apparatus should be isolated in a clean environment to remove the problem of contamination of the surface being measured. This is necessary because the sensitivity of the apparatus to contamination of any kind, and in particular to particulate contamination, is very great. This last effect is a benefit when using the apparatus to detect and locate particles.

While the measurement methods and apparatus herein described constitute preferred embodiments of the invention, it is to be understood that the invention is not limited to the precise methods and apparatus described, and that changes may be made therein without departing from the scope and spirit of the invention as defined in the appended claims.

The invention having thus been described, the following is claimed:

1. A method of simultaneously measuring the distribution of surface and subsurface micro defects on a predetermined area of a material, comprising the steps of:
    (a) generating a beam of electromagnetic radiation with substantially equal S and P polarized components;
    (b) directing the beam towards the surface at a predetermined fixed angle of incidence and focusing the beam to expose a small portion of the material to the electromagnetic radiation;
    (c) directing the lines of sight of two detectors toward the surface of the material to the point where the beam intercepts the surface, one line of sight and detector for only P polarized electromagnetic radiation and the other line of sight and detector for only S polarized electromagnetic radiation;
    (d) limiting the extent of the scattered electromagnetic radiation entering each detector in order to detect the scatter coming from a small solid angle around the line of sight of each detector, for detecting a portion of the scattered electromagnetic radiation and converting it to an electrical signal proportional to the detected intensity from each detector;
    (e) producing relative rotation between the beam and the material about an axis substantially perpendicular to the surface and at the point where the beam intercepts the surface and determining the rotational positions of selected scatter signature for that point;
    (f) producing relative lateral movement between the beam and the material to expose an adjacent portion of the material to the electromagnetic radiation;
    (g) repeating above steps (e) and (f) for each portion of the material exposed until the predetermined area is covered in a contiguous manner; and
    (h) mapping the selected scatter intensity versus the coordinate position of each point of measurement for the predetermined area, the scatter intensity sensed at the P polarization detector being related to the subsurface defects and the scatter intensity sensed at the S polarization detector being related to the surface defects and the rotational positions being related to the defect orientations.

2. A method of simultaneously measuring the distribution of surface and subsurface micro defects on a predetermined area of a material, comprising the steps of:
    (a) generating a beam of electromagnetic radiation with elliptical polarization;
    (b) directing the beam towards the surface at a predetermined fixed angle of incidence and focusing the beam to expose a small portion of the material to the electromagnetic radiation;
    (c) directing the lines of sight of two detectors toward the surface of the material to the point where the beam intercepts the surface, one line of sight and detector for only P polarized electromagnetic radiation and the other line of sight and detector for only S polarized electromagnetic radiation;
    (d) limiting the extent of the scattered electromagnetic radiation entering each detector in order to detect the scatter coming from a small solid angle around the line of sight of each detector, for detecting a portion of the scattered electromagnetic radiation and converting it to an electrical signal proportional to the detected intensity from each detector;

(e) producing relative rotation between the beam and the material about an axis substantially perpendicular to the surface and at the point where the beam intercepts the surface and determining the rotational positions of selected scatter signature for that point;

(f) producing relative lateral movement between the beam and the material to expose an adjacent portion of the material to the electromagnetic radiation;

(g) repeating above steps (e) and (f) for each portion of the material exposed until the predetermined area is covered in a contiguous manner; and (h) mapping the selected scatter intensity versus the coordinate position of each point of measurement for the predetermined area, the scatter intensity sensed at the P polarization detector being related to the subsurface defects and the scatter intensity sensed at the S polarization detector being related to the surface defects and the rotational positions being related to the defect orientations.

3. A method of measuring the distribution of subsurface micro defects caused by random processes such as ion implantation, on a predetermined area of a material, comprising the steps of:

(a) generating a beam of electromagnetic radiation;

(b) directing the beam towards the surface at a predetermined fixed angle of incidence and focusing the beam to expose a small portion of the material to the electromagnetic radiation;

(c) directing the line of sight of the detector toward the surface of the material to the point where the beam intercepts the surface;

(d) limiting the extent of the scattered electromagnetic radiation entering the detector in order to detect the scatter coming from a small solid angle around the line of sight, for detecting a portion of the scattered electromagnetic radiation and converting it to an electrical signal proportional to the detected intensity;

(e) producing relative rotation between the beam and the material about an axis substantially perpendicular to the surface and at the point where the beam intercepts the surface and determining the rotational position of the selected minimum scatter for that point;

(f) producing relative lateral movement between the beam and the material to expose an adjacent portion of the material to the electromagnetic radiation;

(g) repeating above steps (e) and (f) for each portion of the material exposed until the predetermined area is covered in a contiguous manner; and (h) mapping the selected minimum scatter intensity versus the coordinate position of each point of measurement for the predetermined area.

4. Apparatus for simultaneously measuring the distribution of surface and subsurface micro defects on a predetermined area of a material, comprising the steps of:

(a) means for generating a beam of electromagnetic radiation with substantially equal S and P polarized components;

(b) means for directing the beam towards the surface at a predetermined fixed angle of incidence and focusing the beam to expose a small portion of the material to the electromagnetic radiation;

(c) means for directing the lines of sight of two detectors toward the surface of the material to the point where the beam intercepts the surface, one line of sight and detector for only P polarized electromagnetic radiation and the other line of sight and detector for only S polarized electromagnetic radiation;

(d) means for limiting the extent of the scattered electromagnetic radiation entering each detector in order to detect the scatter coming from a small solid angle around the line of sight of each detector, for detecting a portion of the scattered electromagnetic radiation and converting it to an electrical signal proportional to the detected intensity from each detector;

(e) means for producing relative rotation between the beam and the material about an axis substantially perpendicular to the surface and at the point where the beam intercepts the surface and determining the rotational positions of selected scatter signature for that point;

(f) means for producing relative lateral movement between the beam and the material to expose an adjacent portion of the material to the electromagnetic radiation;

(g) means for repeatably engaging means (e) and (f) for each portion of the material exposed until the predetermined area is covered in a contiguous manner; and (h) mean for mapping the selected scatter intensity versus the coordinate position of each point of measurement for the predetermined area, the scatter intensity sensed at the P polarization detector being related to the subsurface defects and the scatter intensity sensed at the S polarization detector being related to the surface defects and the rotational positions being related to the defect orientations.

5. A method of measuring the distribution of micro defects on a predetermined area of a material, comprising the steps of:

(a) generating a beam of electromagnetic radiation;

(b) directing the beam towards the surface at a predetermined fixed angle of incidence;

(c) directing a detector's line of sight toward the surface of the material to the point where the beam intercepts the surface;

(d) detecting a portion of the scattered electromagnetic radiation and converting it to an electrical signal related to the detected intensity;

(e) producing relative rotation between the beam and the material about an axis substantially perpendicular to the surface and at the point where the beam intercepts the surface and determining the rotational position of selected scatter for that point;

(f) producing relative lateral movement between the beam and the material to expose an adjacent portion of the material to the electromagnetic radiation;

(g) repeating above steps (e) and (f) for each portion of the material exposed until the predetermined area is covered in a contiguous manner; and (h) mapping the selected scatter intensity versus the coordinate position of each point of measurement for the predetermined area.

6. Apparatus for measuring the distribution of micro defects on a predetermined area of a material, comprising the steps of:

(a) means for generating a beam of electromagnetic radiation;

(b) means for directing the beam towards the surface at a predetermined fixed angle of incidence;

(c) means for directing a detector's line of sight toward the surface of the material to the point where the beam intercepts the surface;

(d) means for detecting a portion of the scattered electromagnetic radiation and converting it to an electrical signal related to the detected intensity;

(e) means for producing relative rotation between the beam and the material about an axis substantially perpendicular to the surface and at the point where the beam intercepts the surface and determining the rotational position of selected scatter for that point;

(f) means for producing relative lateral movement between the beam and the material to expose an adjacent portion of the material to the electromagnetic radiation;

(g) means for repeatably engaging means (e) and (f) for each portion of the material exposed until the predetermined area is covered in a contiguous manner; and (h) means for mapping the selected scatter intensity versus the coordinate position of each point of measurement for the predetermined area.

* * * * *